US006761561B2

(12) United States Patent
Mandelkern et al.

(10) Patent No.: US 6,761,561 B2
(45) Date of Patent: Jul. 13, 2004

(54) WIRELESS DENTAL CAMERA

(75) Inventors: Stan Mandelkern, Teaneck, NJ (US); Aaron Bratslavsky, Brooklyn, NY (US); Noel Lucas, Bayport, NY (US); David Schick, Flushing, NY (US)

(73) Assignee: Schick Technologies, Long Island City, NY (US)

( * ) Notice: Subject to any disclaimer, the term of this patent is extended or adjusted under 35 U.S.C. 154(b) by 0 days.

(21) Appl. No.: 10/164,007

(22) Filed: Jun. 7, 2002

(65) Prior Publication Data

US 2003/0228553 A1 Dec. 11, 2003

(51) Int. Cl.[7] .............................................. A61C 3/00
(52) U.S. Cl. ...................................... 433/29; 600/112
(58) Field of Search ........................... 433/29; 600/109, 600/110, 112, 160

(56) References Cited

U.S. PATENT DOCUMENTS

| | | | |
|---|---|---|---|
| 4,082,953 A | 4/1978 | Krause et al. ............. 280/413 |
| 4,160,997 A | 7/1979 | Schwartz .................... 358/93 |
| 4,494,950 A | 1/1985 | Fischell ....................... 604/66 |
| 4,575,805 A | 3/1986 | Moermann et al. ......... 364/474 |
| 4,629,424 A | 12/1986 | Lauks et al. .................... 433/6 |
| 4,633,304 A | 12/1986 | Nagasaki ...................... 358/98 |
| 4,658,669 A | 4/1987 | Nishikawa .................... 74/531 |
| 4,835,410 A | 5/1989 | Bhagwat et al. ............. 307/64 |
| 4,858,001 A | 8/1989 | Milbank et al. .............. 358/98 |
| 4,987,897 A | 1/1991 | Funke ......................... 128/419 |
| 5,113,859 A | 5/1992 | Funke ......................... 128/419 |
| 5,115,307 A | 5/1992 | Cooper et al. ................ 358/98 |
| 4,858,001 A | 6/1992 | Milbank et al. .............. 358/98 |
| 5,212,476 A | 5/1993 | Maloney ................. 340/825.19 |
| 5,257,184 A | 10/1993 | Mushabac ............... 364/413.28 |
| 5,264,935 A | 11/1993 | Nakajima .................... 358/181 |
| 5,373,852 A | 12/1994 | Harrison et al. ............. 128/733 |
| 5,434,418 A | 7/1995 | Schick .................. 250/370.11 |
| 5,454,022 A | 9/1995 | Lee et al. ................... 378/98.8 |
| 5,471,518 A | 11/1995 | Barber et al. .................. 379/58 |
| 5,514,873 A | 5/1996 | Schulze-Ganzlin et al. . 250/394 |
| 5,527,261 A | 6/1996 | Monroe et al. .............. 600/109 |
| 5,551,953 A | 9/1996 | Lattin et al. ................... 604/20 |
| 5,712,482 A | 1/1998 | Gaiser et al. ........... 250/363.08 |
| 5,745,165 A | 4/1998 | Atsuta et al. .................. 348/65 |
| 5,873,814 A | 2/1999 | Adair ......................... 600/109 |
| 5,879,289 A | 3/1999 | Yarush et al. ............... 600/179 |
| 5,880,826 A | 3/1999 | Jung et al. ..................... 356/73 |
| 5,908,294 A | 6/1999 | Schick et al. ................. 433/29 |
| 6,106,457 A | * 8/2000 | Perkins et al. .............. 600/175 |
| 6,132,211 A | 10/2000 | Peithman ..................... 433/29 |
| 6,149,300 A | 11/2000 | Greenway et al. .......... 378/191 |
| 6,186,944 B1 | 2/2001 | Tsai ........................... 600/200 |
| 2001/0052930 A1 | 12/2001 | Adair et al. | |

* cited by examiner

Primary Examiner—Cary E. O'Connor
(74) Attorney, Agent, or Firm—Fitzpatrick, Cella, Harper & Scinto

(57) ABSTRACT

A dental camera is provided which is capable of operating in a wireless mode and a wired mode. A handpiece includes circuitry for generating a signal representing a video image and a first connector. A wireless adaptor module includes a power supply for supplying power to the handpiece, a transmitter for transmitting the signal representing a video image, and a second connector that mates with the first connector when the dental camera is being operated in the wireless mode. A cable has a third connector that mates with the first connector when the dental camera is being operated in the wired mode. With this system, clinical flexibility is afforded to a dental practitioner.

19 Claims, 9 Drawing Sheets

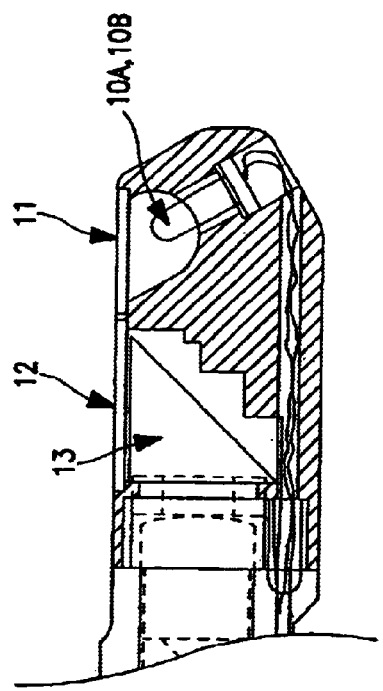 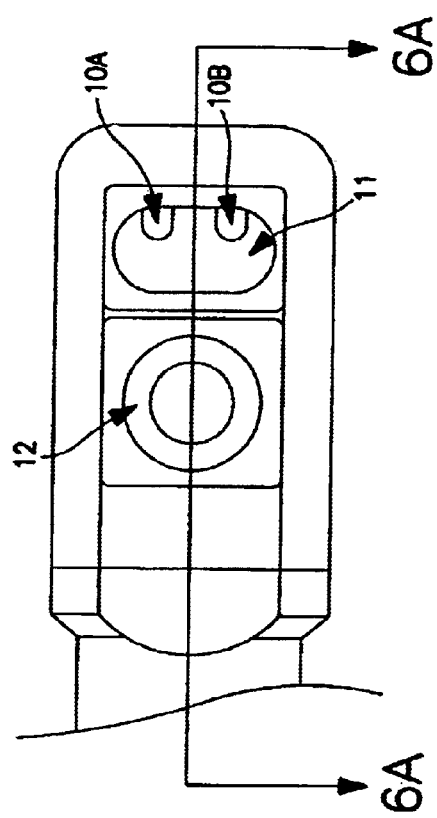

WIRELESS DENTAL CAMERA

BACKGROUND OF THE INVENTION

1. Field of the Invention

This invention relates generally to the field of dental cameras, and more particularly to an intra-oral dental camera system which can be switched easily between wireless and wired modes of operation.

2. Related Art

For many years, dental practitioners used dental mirrors to more clearly visualize and diagnose difficult to see areas in a patient's mouth. Dental mirrors remain useful in certain respects, but significant limitations exist. First, it is often difficult using mirrors to visualize a dental structure, because the image must be reflected into the practitioner's line of sight. Second, mirrors provide a relatively small image that can be difficult to see, particularly for older practitioners. Third, providing the lighting necessary to properly and fully illuminate the area being reflected by the mirror is often difficult. Furthermore, it is often very difficult using mirrors to communicate information to the patient or to other practitioners because the image that is being visualized depends upon the viewer's position relative to the mirror. Moreover, mirrors do not provide a permanent record of what a dental practitioner sees.

In order to address these and other significant limitations associated with using mirrors to visualize and diagnose obscure areas of a patient's mouth, intra-oral cameras were introduced into the field, and are now widely used in the dental industry to enhance the dental practitioner's ability to view the inside of a patient's mouth. Intra-oral dental cameras are also useful in providing the patient with a visual understanding of his or her clinical options, and in obtaining a permanent record of the condition of the patient's mouth.

Existing dental cameras provide advantages over dental mirrors in several respects. First, they do not require positioning towards a reflected angle. Also, they can be used as "teaching tools" to communicate information to others, since more than just the dentist may view their output.

Moreover, many dental cameras have built-in light sources that illuminate the area being photographed. U.S. Pat. No. 5,908,294 to Schick et al., for example, discloses a dental imaging system including a handheld video camera that uses a white LED to illuminate the subject. The camera allows for a slimmer instrument, a feature that is preferred clinically because of easier access to places that thicker instruments cannot reach.

The first dental cameras were simply adaptations of video endoscopes used in the field of medicine. U.S. Pat. No. 4,858,001 to Milbank et al. provides an example of an early dental camera. Milbank et al. discusses a hand-held endoscopic apparatus consisting of a body, a camera, and a removable and interchangeable image-gathering element capable of presenting an image of an object to the camera. The image-gathering element, also called an objective element, may enable viewing of an image at varying angles because the objective element may be flexible or rigid and may be of a variety of sizes and shapes. The objective element connects to a handpiece which has a hollow or tubular body portion rotatably carrying a central shaft upon which is mounted a video camera arrangement such as a CCD mosaic chip camera. The tubular design is suited for penetration into the convoluted cavity of the human body.

U.S. Pat. No. 5,115,307 to Cooper discloses an electronic video dental camera which includes a handle and a camera head located at the distal end of the handle. The camera head is formed at an angle to the handle in order to provide the same general shape of dental mirrors, and includes light sources for illuminating the area to be viewed. Circuitry may be located in the handle, cable, or connectors.

Today's wired dental cameras typically have a handpiece which contains an image sensor and optics. The cameras also typically have a base station which provides power, light, and video processing. A connection is required to deliver the power and light from the base station to the handpiece. This is usually achieved by providing a cable that has both electrical and optical conductors. The light is often delivered by way of a flexible fiber optic bundle.

Wired dental cameras, although more advantageous in many respects than dental mirrors, as explained above, also have a number of limitations. Some of these limitations are due to the inconvenience caused by the cable. The cable presents several problems. First, it limits the distance between the base station and the handpiece. Second, it limits the portability of the system, making it difficult to transport the system between rooms and such. Third, it causes the handpiece to be more cumbersome and therefore harder to maneuver within a patient's mouth.

Existing wireless cameras directed to dental applications attempt to address these and other drawbacks, although certain limitations with these types of cameras also exist. For example, although some prior art systems relating to wired cameras use optical fibers to direct light from the base station to the handpiece, in a wireless camera, the light source must be integral to the handpiece. Some prior art wireless systems are equipped with a lamp which is placed at the end of the imaging head, but such design usually results in a camera body which is too large. It is desirable for a dental camera design to adhere to practical limits relating to size and weight. In addition, the handpiece of the wireless dental camera should include a light source, a power source, and a transmitter.

Thus, despite their advantages, wireless cameras will necessarily be heavier than wired ones, since they need to incorporate a transmitter and a power supply. There are times, therefore, when a dental practitioner might prefer a wired camera over a wireless one. Accordingly, the optimal intra-oral camera would be switchable between those two modes.

U.S. Patent Application Publication No. US 2001/0052930 A1 to Adair et al. is directed to a reduced area imaging device, such as an endoscope, and teaches a wired and a wireless embodiment; however, it does not show a single device that is switchable between wired and wireless modes of operation.

U.S. Pat. No. 5,879,289 to Yarush et al. relates to a hand-held portable endoscopic camera that purports to be capable of operating in either of a cordless or corded mode. However, Yarush et al. eliminates the cord by providing in a self-contained, allegedly hand-held apparatus lens means, video image means, light source means, and power supply means, along with a liquid crystal display monitor 36 on which the images may be viewed. The inclusion of such a monitor on the handpiece makes it a heavy and cumbersome device. Moreover, some of the inherent advantages of a dental camera, such as for example the ability to allow multiple people, including the patient, to easily view the images, are mitigated substantially. Furthermore, in another embodiment of Yarush et al., the camera is electrically coupled to the contents of a supplemental casing to be held in a practitioner's hand or mounted on the practitioner's belt.

The case contains power supply means, light source means, video imaging means, transmitter means, and/or display means. Therefore, a wire still protrudes from the patient's mouth in order to connect to the supplemental casing.

There exists, therefore, a great need for a dental camera which overcomes the above-mentioned problems of the prior art. The technique should ideally provide a dental camera which is lighter in weight, less bulky, easier to maneuver within a patient's mouth, and more portable than prior art systems.

SUMMARY OF THE INVENTION

The present invention provides an intra-oral dental camera system that is capable of being operated in both wireless and wired modes, and that can be switched easily between the two. Both the wireless and the wired modes interface through a common connector. In the wired mode, the camera is connected to an image processing system, such as a computer, via a cable attached to the connector. In the wireless mode, the connector is removed from the cable and is attached to a wireless adaptor module containing supplemental components such as a battery and a transmitter, allowing for convenient and unconfined operation. With this system, clinical flexibility is afforded to the dental practitioner.

It is an object of this invention to provide a removable wireless adaptor module which is placed integral but distal to the dental camera. In this way, the dental camera may be used either in the wired mode for a lighter tool and for a continuous mode of operation during a longer procedures or in the wireless mode for less restricted maneuverability. The wired mode is effected simply by removing the connector from the wireless adaptor module and plugging it into a cable.

Therefore, the dental camera may be used either with a cable or with a removable RF module. This provides the practitioner with the flexibility to use the camera in the mode which is most effective for the particular situation and which is most preferable to the practitioner.

It is therefore object of this invention to overcome the problems of the prior art discussed above by providing a dental camera which is lighter in weight, smaller in size, less bulky, and more portable than prior art systems.

It is also an object of this invention to provide a dental camera capable of being switched easily between wired and wireless modes and which has a light source to illuminate dental structures in a patient's mouth. The preferred embodiment employs an LED light source.

It is also an object of this invention to provide a camera attachment for receiving the transmitter circuitry and battery pack.

In accordance with the teachings of the present invention, these and other objects may be accomplished by the present invention, which is a dental camera system which can be switched easily between wireless and wired modes of operation The invention in one embodiment provides a dental camera capable of operating in a wireless mode and a wired mode. A handpiece includes means for generating a signal representing a video image and a first connector. A wireless adaptor module includes a power supply for supplying power to the handpiece, a transmitter for transmitting the signal representing a video image, and a second connector that mates with the first connector when the dental camera is being operated in the wireless mode. A cable has a third connector that mates with the first connector when the dental camera is being operated in the wired mode.

The transmitter transmits the signal representing a video image to an image processing unit via a wireless link when the dental camera is being operated in the wireless mode. The cable is connected to the image processing unit when the dental camera is being operated in the wired mode. The cable supplies power to the handpiece when the dental camera is being operated in the wired mode. The power supply may be a rechargeable battery. The first connector may be located on a proximal end of the handpiece.

The invention in another embodiment provides a dental camera system capable of operating in a wireless mode and a wired mode for transmitting a signal representing a video image to an image processing unit. A handpiece includes means for generating a signal representing a video image, and includes a first connector. A wireless adaptor module includes a power supply for supplying power to the handpiece, a transmitter for transmitting the signal representing a video image to the image processing unit, and a second connector that mates with the first connector when the dental camera is being operated in the wireless mode. A cable includes a third connector that mates with the first connector for supplying power to the handpiece and for delivering the signal representing a video image to the image processing unit when the dental camera is being operated in the wired mode.

The invention in another embodiment provides a dental camera capable of operating in a wireless mode and a wired mode. A handpiece includes means for generating a signal representing a video image and a first connector that mates with a second connector of a wireless adaptor module when the dental camera is being operated in the wireless mode, and that mates with a third connector of a cable when the dental camera is being operated in the wired mode.

The invention in another embodiment provides a dental camera system switchable between a wireless mode and a wired mode. A handpiece having a proximal end and a distal end includes a light source located on a distal end for illuminating a subject, a window, located near the light source, for receiving light reflected from the subject, light direction means for directing the received light in the proximal direction, an image sensor located on the proximal side of the light direction means, for receiving the directed light, and a first connector located on the handpiece. An image processing unit generates a video signal based on outputs of the image sensor. A wireless adaptor module for operating during the wireless mode includes a power supply for supplying power to the handpiece, a transmitter for transmitting outputs of the image sensor to the image processing unit, and a second connector that mates with the first connector when the dental camera is being operated in the wireless mode. A cable is included for operation during the wired mode, connected to the image processing unit, for supplying power to the handpiece and for delivering outputs of the image sensor to the image processing unit, the cable having a third connector that mates with the first connector when the dental camera is being operated in the wired mode. The image sensor may be a charge-coupled device or an active pixel sensor array.

The invention in another embodiment comprises a dental camera switchable between a wireless mode and a wired mode. A handpiece includes means for generating a signal representing a video image and first connecting means. A wireless adaptor module includes power supply means for supplying power to the handpiece, transmitting means for transmitting the signal representing a video image, and second connecting means that mates with the first connecting means when the dental camera is being operated in the wireless mode. A cable has third connecting means that mates with the first connecting means when the dental camera is being operated in the wired mode.

The invention will next be described in connection with certain exemplary embodiments; however, it should be clear to those skilled in the art that various modifications, additions, and subtractions can be made without departing from the spirit or scope of the claims.

BRIEF DESCRIPTION OF THE DRAWINGS

The invention will be more clearly understood by reference to the following detailed description of exemplary embodiments in conjunction with the accompanying drawings, in which:

FIG. 6A is a cross-sectional view of a distal fragmented portion of the camera taken from section line 3A—3A in FIG. 6B according to one embodiment;

FIG. 6B is a bottom view of the distal fragmented portion of the camera according to the embodiment of FIG. 6A;

DETAILED DESCRIPTION OF THE INVENTION

The present invention provides an intra-oral dental camera system that is capable of being operated in both wireless and wired modes and that can be switched easily between the two. Both the wireless and the wired modes interface through a common connector. In the wired mode, the camera is connected to an image processing system, such as a computer, via a cable attached to the connector. In the wireless mode, the connector is removed from the cable and is attached to a wireless adaptor module containing supplemental components such as a battery and a transmitter, which communicates with the image processing system through a wireless link, such as for example through a radio frequency (RF) link. With this system, clinical flexibility is afforded to the dental practitioner.

Figure 1:
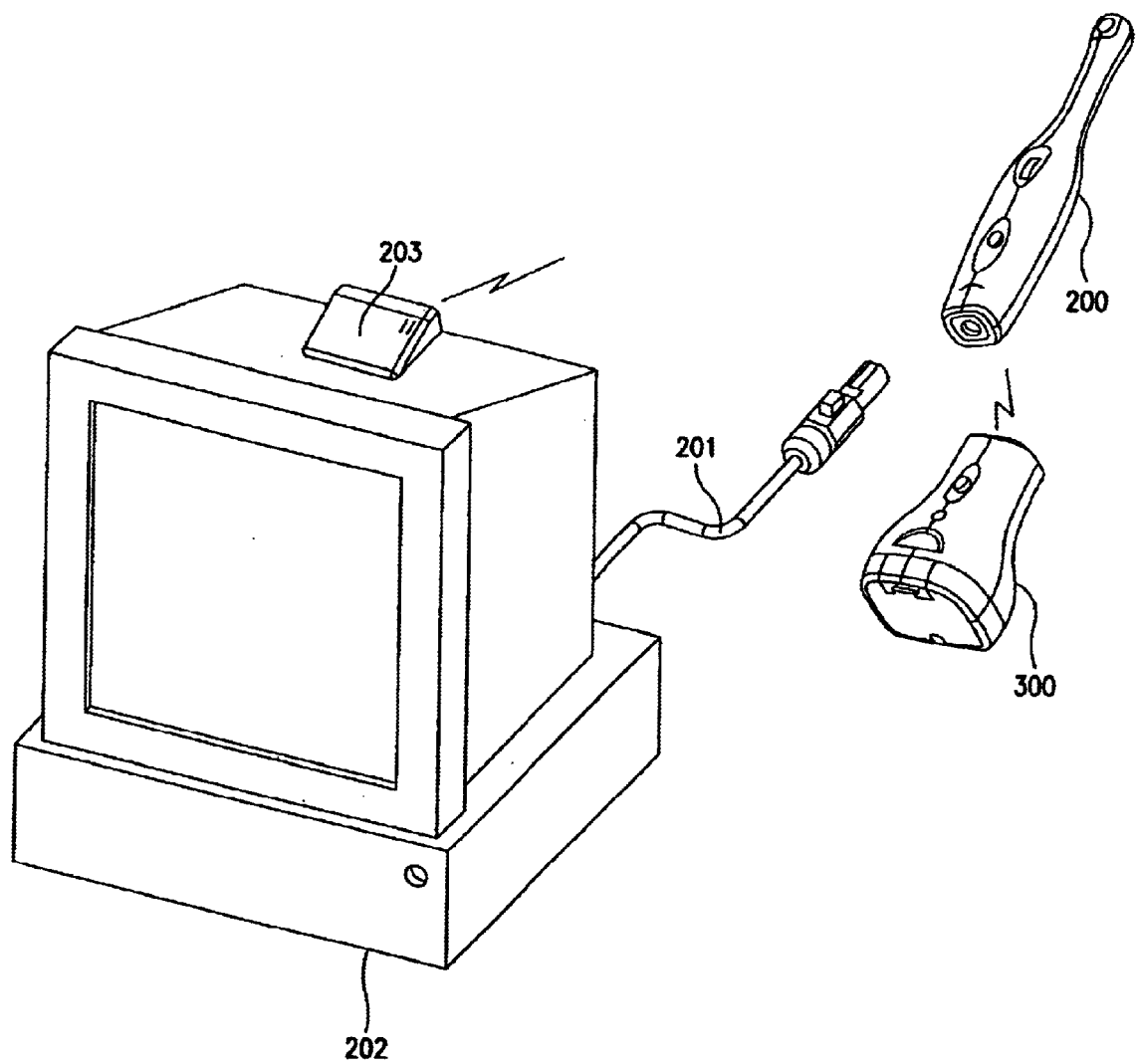
FIG. 1 illustrates the dental camera of this invention capable of being switched between the wired and wireless modes according to one embodiment.

FIG. 1 illustrates a detachable wireless dental camera capable of being switched between the wired and wireless modes according to one embodiment of the invention. As shown, the dental camera includes an intra-oral dental handpiece 200 having a connector that can connect to either a cable 201 or a wireless adapter module 300. In this way, the camera may be switched easily between the two modes. The handpiece 200 communicates with an image processing system 202 via either the cable (or connecting cord) 201 in the wired mode or the wireless adaptor module 300 in the wireless mode. The connector in the embodiment shown in FIG. 1 includes an adjustable knob to secure the connection.

Figure 2:
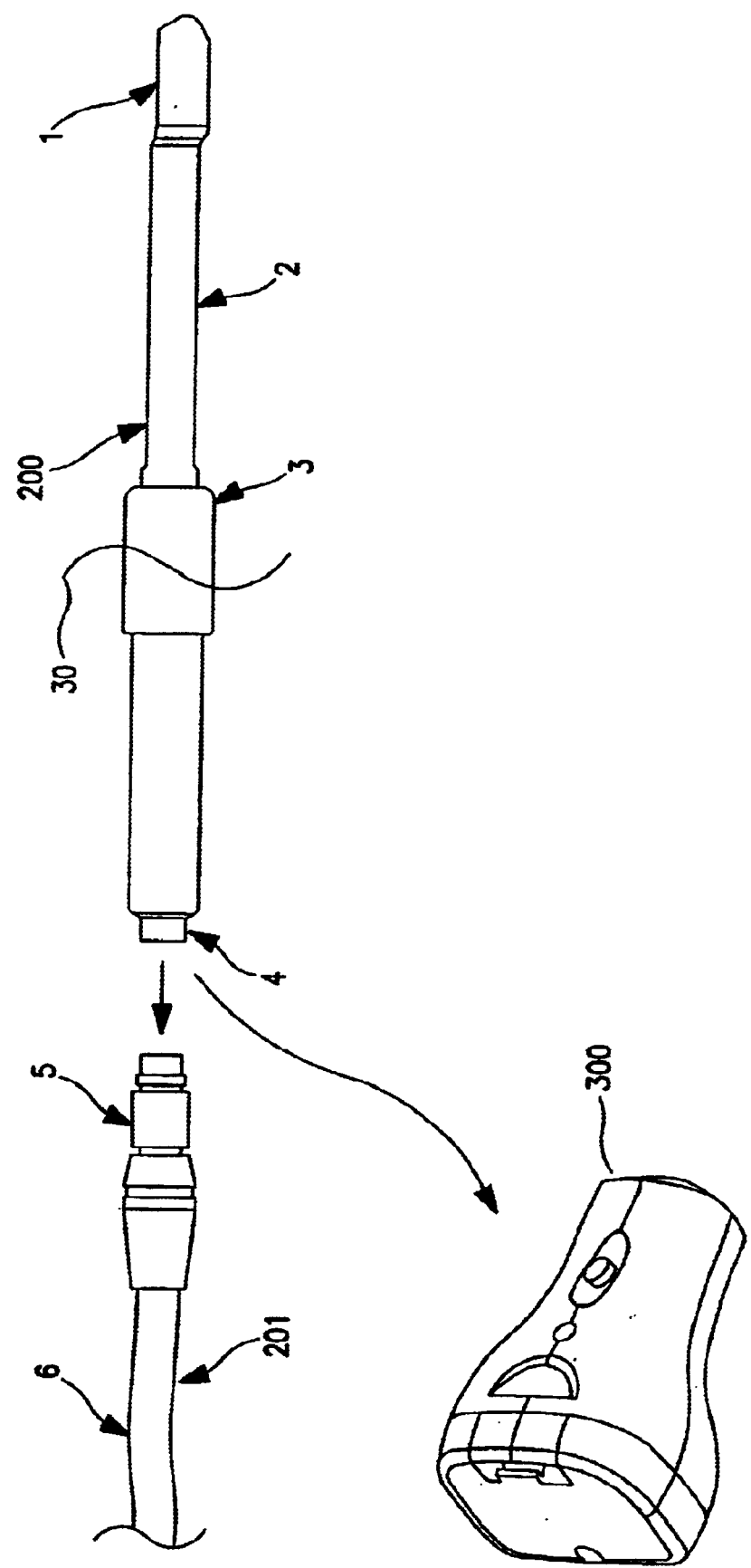
FIG. 2 is a side view of the camera showing the handpiece capable of being attached to either the cable or the wireless adaptor module according to one embodiment.

FIG. 2 is an external side view of the camera showing the handpiece 200 capable of being attached to either the connecting cord 201 or the wireless adaptor module 300. It is noted that the connecting means shown in FIG. 2 is of a different embodiment from that of FIG. 1, as various embodiments may be imagined. The handpiece 200 shown in FIG. 2 has a distal end 1, a median section 2, a focusing ring 3, and a mini circular connector 4 at the proximal end of the handpiece. In the embodiment shown, reference numeral 30 indicates that the focusing ring 3 can be manually rotated. In the wired mode, the mini circular connector 4 mates with a matching mini circular connector 5 located at the end of the cable 6. Signals originating from an image sensor (not shown) housed inside the handpiece 200 travel through the connector 4, the connector 5, and the cable 6 on their way to the image processing system. In the wireless mode, the mini circular connector 4 mates with a matching connector of the wireless adaptor module 300. Signals originating from the image sensor (not shown) housed inside the handpiece 200 travel through the connector 4 to the wireless adaptor module 300 via the matching connector 302 and are transmitted to a receiver 203 of the image processing system 202 by way of a transmitter 304 (shown in FIG. 3) located on the wireless adaptor module 300.

Figure 3:
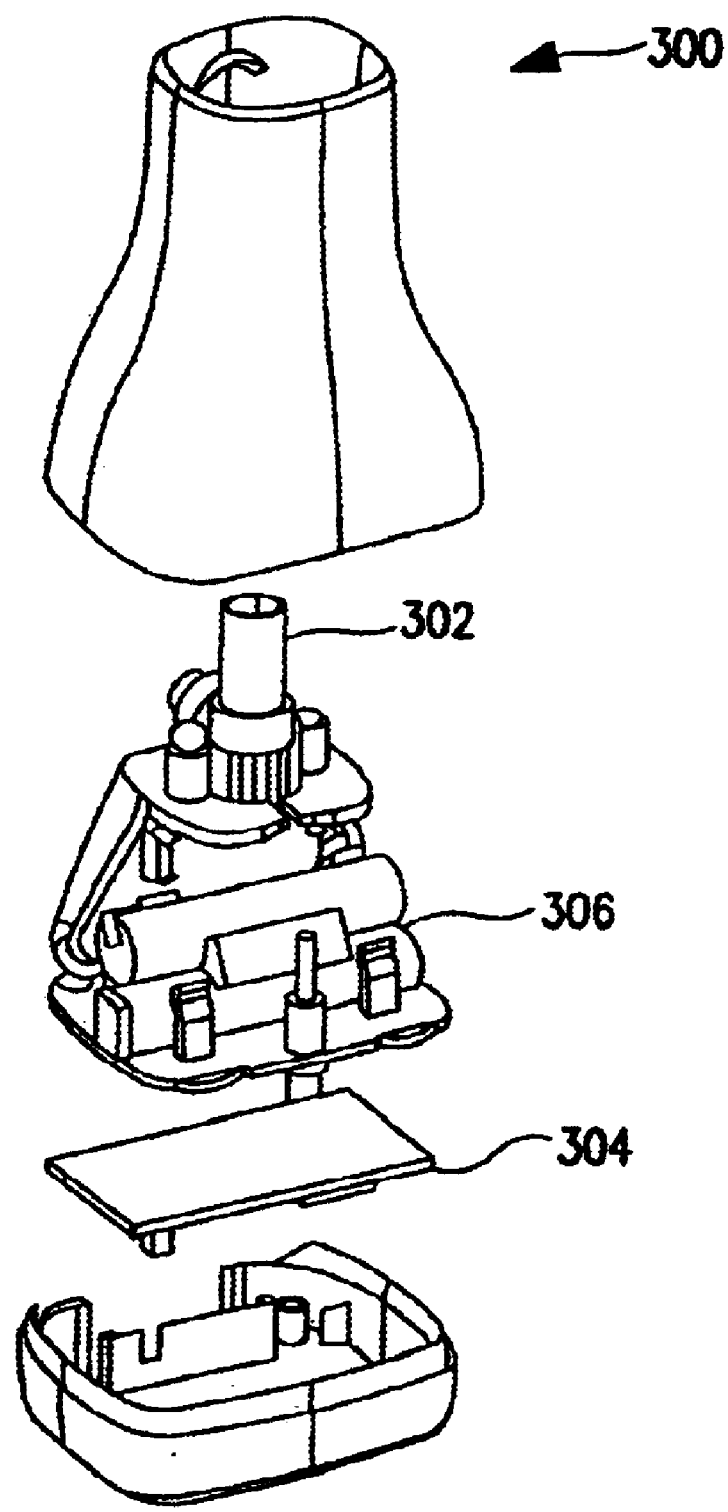
FIG. 3 is an exploded assembly drawing of the wireless adaptor module used in the wireless mode according to one embodiment.

The wireless mode of operation will now be discussed. FIG. 3 is an exploded assembly drawing of the wireless adaptor module according to one embodiment. The wireless adaptor module 300 includes a connector 302 which mates with the connector 4 of the handpiece 200, an RF transmitter 304, and a battery 306. Of course, various embodiments may be envisioned. For example, placing additional components in the wireless adaptor module 300 can lead to a decrease in the size and weight of the handpiece, among other benefits. An advantage of this invention is that the wireless module 300 can be connected directly to the handpiece 200 using the same type of connector used by the cable 201 in the wired application. The connector 302 contains a mechanical interlock to ensure that the wireless adaptor module 300 is secure. Other methods of connecting and securing the wireless adaptor module 300 can be readily envisioned by those skilled in the art. It is important to note that while attaching the wireless module 300 results in the distal end of the handpiece becoming longer, the size of the portion that enters the patient's mouth is the same. This avoids the problem whereby an excessively large and bulky handpiece enters the patient's mouth.

The video processing circuitry produces an NTSC signal which can easily be modulated by the RF transmitter 304. In a preferred embodiment, the RF unit 304 transmits at a frequency of 900 MHz, although other transmitters could be employed by those skilled in the art. In the embodiment shown in FIG. 3, a receiver 203 (see FIG. 1) should be located within approximately 50 feet of the transmitter. The receiver 203 demodulates the RF signal and produces a reconstructed NTSC signal, which may be fed into any standard video display or capture device. In other embodiments, a PAL, SECAN, or digital video signal could be used.

Figure 4:
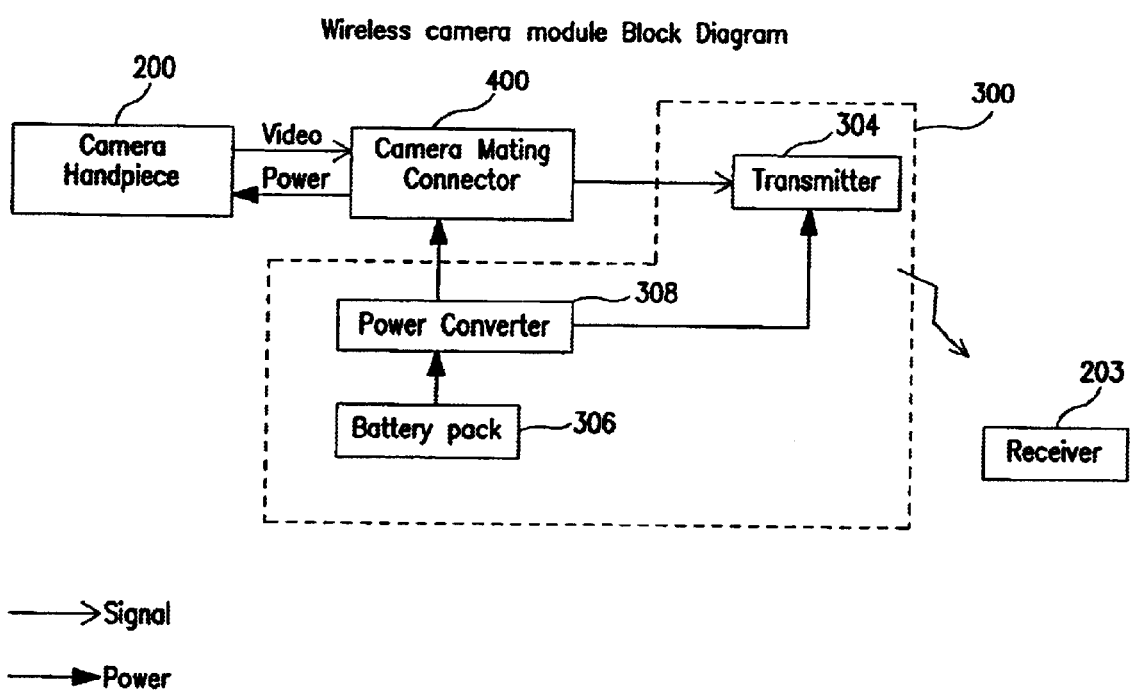
FIG. 4 is a block diagram showing the internal components of the camera according to one embodiment.

FIG. 4 is a block diagram showing the internal circuitry of the camera according to one embodiment. The camera handpiece 200 is connected to the wireless adaptor module 300 via a camera mating connector 400, which, as explained above, could consist of a number of various embodiments. The wireless adaptor module 300 of this embodiment includes a transmitter 304, a battery pack 306, and a power converter 308. Signals originating from the image sensor (not shown) housed inside the handpiece 200 travel through the camera mating connector 400 to the wireless adaptor module 300 and are transmitted to the receiver 203 of the image processing system by way of the transmitter 304.

The wireless adapter module 300 may be powered by a rechargeable dual cell NiCd battery, which may be disposed of and replaced at a low cost. The battery can be charged in a relatively short time, roughly 1.5 hours, and can hold this full charge for about 30 minutes of continuous use. Typical clinical use of the camera is approximately 3–5 minutes per patient and can be resumed after the battery is replenished by placing it in the charger for 15 minutes or so. This should not be an inconvenience because such downtime is available between patients. If the dental practitioner's protocol greatly exceeds this usage pattern, he or she may alternatively use the corded mode of operation. Of course, alternate portable power sources such as an utra cap or primary battery can be readily envisioned by those skilled in the art.

Figure 5:
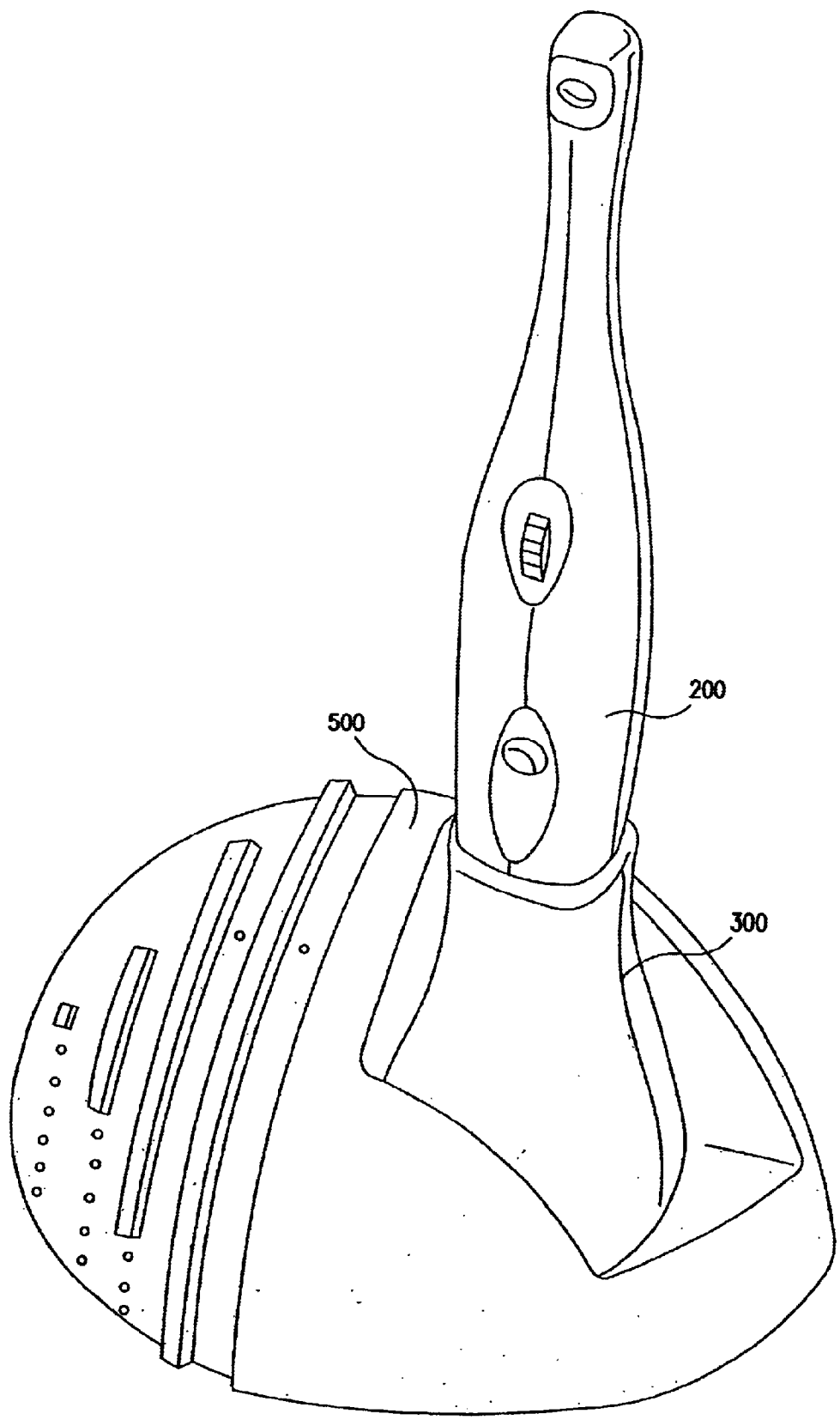
FIG. 5 is an illustration of a preferred embodiment including the charger.

FIG. 5 is an illustration of a preferred embodiment including the charger 500. On the bottom of the wireless adaptor module 300 is a connector that interfaces with the recharging device 500. The antenna (not shown) for the transmitter is located at the very bottom of the wireless adaptor module 300, and is designed to be located beyond the area where the user would normally grip the camera in use. In this way, the chance of a user's hand blocking the RF signal is reduced. The wireless adaptor module 300 interfaces with the charging device by way of a recessed connector.

FIGS. 6A and 6B show details of the distal end 1 of one embodiment of the handpiece, which includes an imaging window 12 and light sources 10a and 10b. The imaging window receives light reflected by the subject. The light sources 10a and 10b, which are located distal to the imaging window 12 and are covered by a protective glass shield 11, are aimed so that they will provide illumination for subjects located below the window. A prism 13 is located within the distal end 1 of the handpiece, angled in relation to the imaging window 12 to direct the light arriving through the imaging window in the direction of the proximal end of the handpiece. Of course, instead of using an individual imaging window 12 and shield 11, as depicted in the figure, a single piece of material may be used as both the window and the shield. In this configuration, the material would have a window portion and a shield portion distal to the window portion. Other variations are possible as well.

A wide variety of lamps may be used. A low-power, long life lamp is preferable to save power and minimize service calls and system down time. One example of a suitable lamp is an incandescent light bulb, such as Gilway Technical Lamp #4115. Another example is a white LED. This white LED could comprise, for example, a short-wavelength LED combined together with a phosphorescent coating, such as Nichia America #NSCW-100. The white LED could also comprise, for example, a set of three single color LEDs (e.g., red, green, and blue), mounted in a single package, such as Nichia America #NSCM-310. While two lamps are depicted in the figure, any number of lamps may be used.

In addition to generating light, the lamps also generate some heat. This is advantageous in dental applications, because it helps clear away condensation that could form from a patient's breathing on a cold instrument.

By locating the lamps in the distal end of the handpiece, distal to the imaging window, and angling the lamps so as to provide direct illumination of the object being imaged, the diameter of the housing can be minimized. This allows the device to be contained within a slimmer housing, as compared to cameras which have light sources positioned above the imaging window.

Figure 9D:
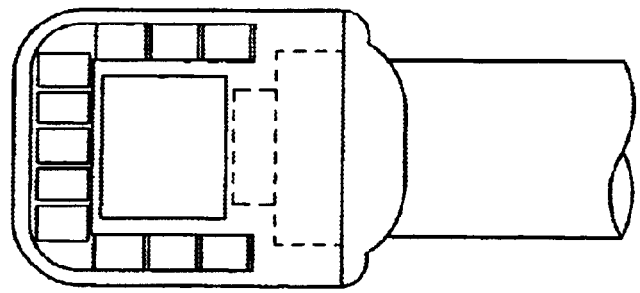
FIGS. 9A–9D show alternate arrangements of lamps about the imaging window.
Figure 9C:
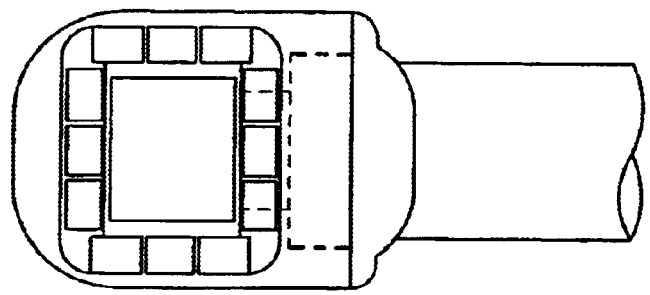
Figure 9B:
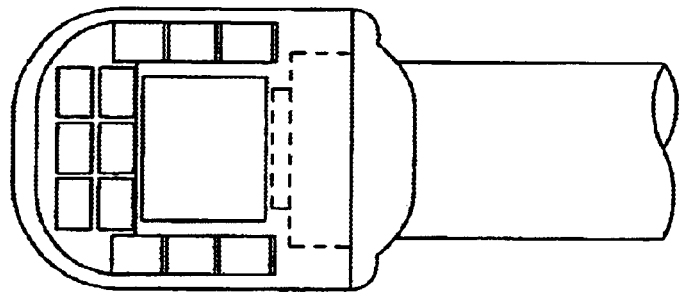
Figure 9A:
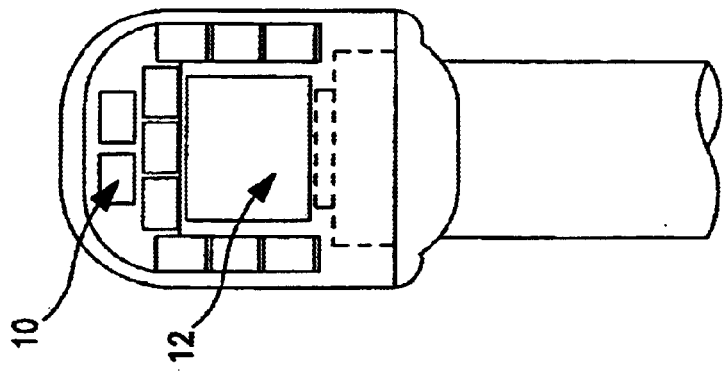

Alternative light source arrangements may also be used. For example, FIGS. 9A, 9B, and 9D show a number of light sources 10 arranged on three sides of the imaging window 12. FIG. 9C shows a number of light sources arranged on four sides of the imaging window. Numerous other light source arrangements can be readily envisioned.

Aiming of the light sources depends on both the arrangement of the light sources around the window and the type of light source used. For example, when incandescent lamps are used in the configuration shown in FIG. 6B, the lamps should be angled as shown in the figure so that the light is directed back towards the proximal end. When LEDs are used in any of the configurations depicted in FIGS. 9A–9D, the LEDs can be aimed perpendicular to the surface of the instrument, because the light is sufficiently diffused to illuminate the subject.

Figure 7:
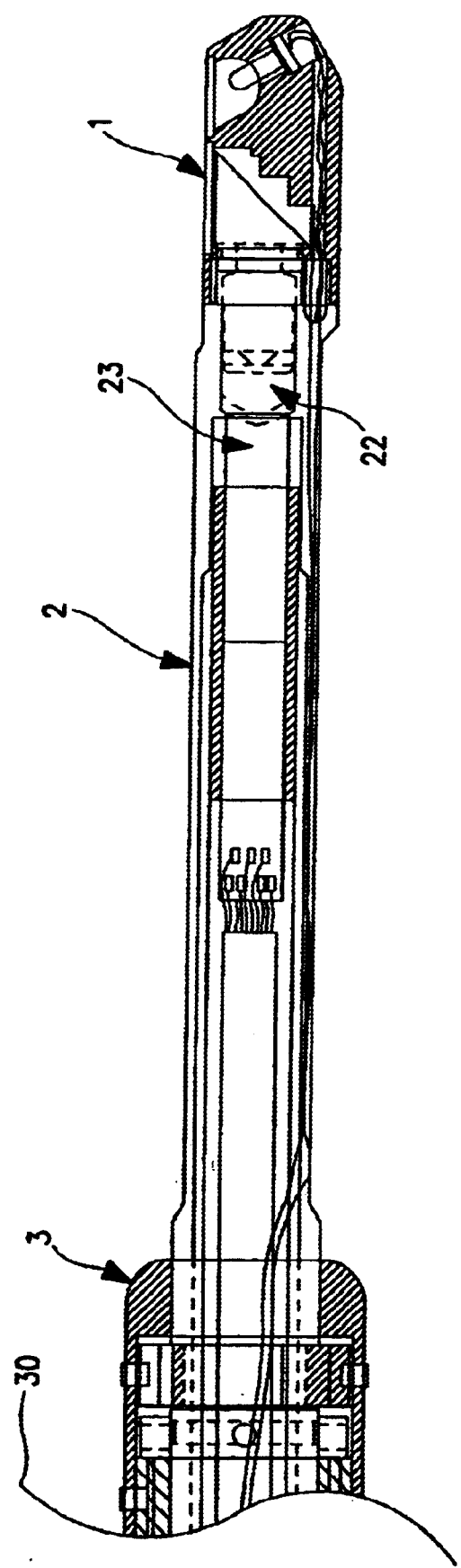
FIG. 7 is a cross-sectional view of the camera, showing detail in the median portion according to one embodiment.

FIG. 7 is a cross-sectional view of the camera according to one embodiment, showing details of the median section 2 of the handpiece, which houses the lens system 22, the image sensor 23, and the focusing mechanism 3. The lens system 22 is preferably a fixed-focus lens system. The image sensor 23 is preferably either a CCD (charge coupled device) or a CMOS APS (active pixel sensor array).

The lens system 22 is located in the distal portion of the median section 2, proximal to the distal end 1 of the handpiece. The movable image sensor 23 is located proximal to the fixed lens system 22. The lens system 22 transmits the light arriving from the distal end 1 of the handpiece to the active surface of the image sensor 23. The lens system 22 may be replaced by another type of light direction means including, for example, a mirror, a prism, and an optical fiber.

The movable image sensor 23 is controlled by a plunger system which is attached to the focusing ring 3. Preferably, the focusing ring 3 can be manually rotated into any of a plurality of detented positions that correspond to a plurality of image sensor positions.

One preferred embodiment uses four detented positions. When the focusing ring 3 is rotated into each of the four various positions, the image sensor, which is mechanically coupled to the plunger system, is moved nearer to or farther from the fixed lens system 22 along a proximal-to-distal axis, depending on the degree of rotation. Each of these positions has an associated focal setting and depth of field. In one embodiment, the approximate focal range settings are: (1) 1 to 6 mm; (2) 5–15 mm; (3) 12–25 mm; and (4) 180 mm through infinity. This selection of focal range settings may be optimized for dental imaging by minimizing the required amount of manipulation while maximizing image quality and ease of use. For a system using a 3.65 mm×2.74 mm rectangular CCD image sensor and a lens with a focal length of 4.50 mm, the total range of movement of the image sensor needed to obtain these focal settings is approximately 2 mm. If the amount of light supplied to the subject is increased, the depth of field can be extended by reducing the aperture of the lens. This would allow a reduction in the number of focus ranges.

Figure 8:
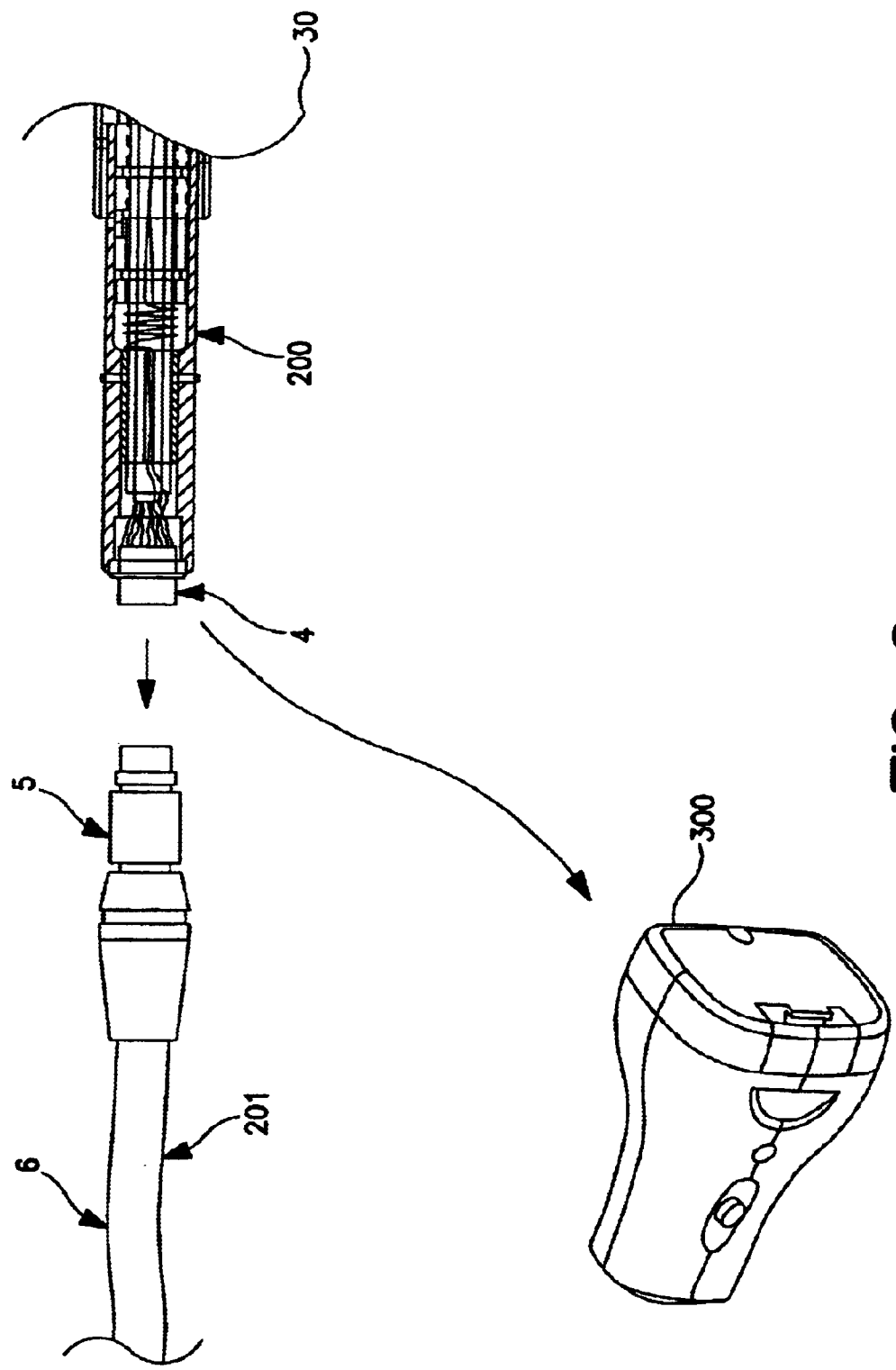
FIG. 8 is a view of the proximal portion of the handpiece and the distal portion of the connecting cord assembly for the wired mode and the wireless adaptor module for the wireless mode, according to one embodiment.

FIG. 8 shows a sectional view of the proximal end of the handpiece 200, as well as the distal end of the connecting cord assembly 201 for the wired mode, and the wireless adaptor module for the wireless mode, according to one embodiment. The mini circular connector 4 at the proximal end of the handpiece 200 mates with the connector 5 on the connecting cord assembly 201 for the wired mode. Preferably, the connectors can be mated and released quickly. A suitable connector pair for this purpose includes, for example, parts Nos. HR25-9P-16 and HR25-9R16 made by Hirose Electric. The connecting cord assembly 201 includes a cable 6 which is preferably flexible and lightweight. When the connector 4 is mated with the connector 5, the connecting cord assembly transmits the video image acquired by the image sensor in the handpiece to the image processing system (shown in FIG. 1). Some preprocessing (including, e.g., preamplification) may be performed by known means in the handpiece 200 before the image signals are sent to the image processing system. In the wireless mode, the connector 4 mates with the connector 302 of the wireless adaptor module 300.

Returning to FIG. 1, the image processing system 202 may be implemented in hardware, software or a combination of both. Two image processing settings may be selected: intraoral and extraoral. These settings correct for the quality and amount of light available and allow for realistic images to be acquired in both intraoral and extraoral locations, because ambient light is qualitatively different from lamp light. This feature is implemented by storing two different white balances in the image processing system (one for the extraoral setting and one for the intraoral setting) and processing the image using the appropriate stored white balance. The white balance processing adjusts the levels of the red, green, and blue components of the image to create an image in which white objects are perceived as being white.

A preferred approach of implementing the white balance processing uses the Panasonic GP-KS 162 CB camera control unit (CCU) together with a Panasonic GP-KS 462HM CCD. The CCU includes circuitry to interface with the CCD, white balance processing, and circuitry to generate an NTSC video signal. The CCU can store two white balances corresponding to two different types of light. For example, the white balance settings for the ambient light coming from a dentist's overhead light and from the camera's light source can be stored. When the dentist uses the camera, the appropriate white balance setting can be selected instantaneously without recalibrating the white balance for each exposure.

The preferred CCU can compensate for white balances ranging from 2,200–10,000 degrees K of color temperature. Incandescent lamps and both types and white LEDs are available within that temperature range. For those parts that have a wide range of color temperature, samples with the appropriate color temperature should be selected.

In the case of intra-oral imaging, very little ambient light is available. When the camera is switched to the intra-oral setting, the light source located in the head of the camera can be automatically switched on. In this mode, the image is processed using a stored white balance corresponding to the quality of the lamps which provide illumination (e.g., the incandescent bulbs or LEDs described above). In the case of extra-oral imaging, ambient light is available. When the camera is switched to the extra-oral setting, the light source can be automatically turned off. Due to the presence of ambient light, a different stored white balance is used to process the image.

The embodiments described above involve illuminating the subject with white light and detecting the light using a sensor that is sensitive to white light. An alternative embodiment uses a monochromatic sensor and strobes of different colored monochromatic light to attain the same effect as white illumination. In other words, instead of illuminating the subject with white light, the subject is strobed with each of the components of white light (red, green, and blue) sequentially. During each strobe period, the output from the image sensor is captured. The image sensor outputs from the three strobe periods are then combined by a signal processor to form a standard RGB video signal. It is also possible to implement an equivalent system by illuminating the subject with more than one color at a time. For example, red light may be used during the first phase, and red and blue light may be used during the second phase. Then, the blue component may be computed by subtraction. Of course, other combinations of colors may be used as well. By using this system, a monochromatic image sensor may be used in place of a full color image sensor. This is advantageous because monochromatic image sensors are significantly less expensive.

The combination of features described above allows the camera to be lighter, more portable, consume less power, and to produce a more authentic image than previous cameras.

While the invention has been particularly shown and described with respect to preferred embodiments thereof, it will be understood by those skilled in the art that changes in form and details may be made therein without departing from the scope and spirit of the invention.

Having described the invention, what is claimed as new and secured by Letters Patent is:

1. A dental camera capable of operating in a wireless mode and a wired mode, comprising:
   a handpiece having means for generating a signal representing a video image and a first connector;
   a wireless adaptor module having a power supply for supplying power to the handpiece, a transmitter for transmitting the signal representing a video image, and a second connector that mates with the first connector when said dental camera is being operated in the wireless mode; and
   a cable having a third connector that mates with the first connector when said dental camera is being operated in the wired mode.

2. The dental camera as set forth in claim 1, wherein the transmitter transmits the signal representing a video image to an image processing unit via a wireless link when said dental camera is being operated in the wireless mode.

3. The dental camera as set forth in claim 2, wherein the cable is connected to the image processing unit when said dental camera is being operated in the wired mode.

4. The dental camera as set forth in claim 1, wherein the cable supplies power to the handpiece when said dental camera is being operated in the wired mode.

5. The dental camera as set forth in claim 1, wherein the power supply comprises a rechargeable battery.

6. The dental camera as set forth in claim 1, wherein the first connector is located on a proximal end of the handpiece.

7. The dental camera as set forth in claim 6, wherein the first connector is located on a proximal end of the handpiece.

8. A dental camera system capable of operating in a wireless mode and a wired mode for transmitting a signal representing a video image to an image processing unit, comprising:

a handpiece having means for generating a signal representing a video image, and having a first connector;

a wireless adaptor module having a power supply for supplying power to the handpiece, a transmitter for transmitting the signal representing a video image to the image processing unit, and a second connector that mates with the first connector when said dental camera is being operated in the wireless mode;

a cable having a third connector that mates with the first connector for supplying power to the handpiece and for delivering the signal representing a video image to the image processing unit when said dental camera is being operated in the wired mode.

9. The dental camera system as set forth in claim 8, wherein the power supply comprises a rechargeable battery.

10. A dental camera system switchable between a wireless mode and a wired mode, comprising:

a handpiece having a proximal end and a distal end, and having
a light source located on a distal end for illuminating a subject;
a window, located near the light source, for receiving light reflected from the subject;
light direction means for directing the received light in the proximal direction;
an image sensor located on the proximal side of the light direction means, for receiving the directed light; and
a first connector located on the handpiece;

an image processing unit for generating a video signal based on outputs of the image sensor;

a wireless adaptor module for operating during the wireless mode, having:
a power supply for supplying power to the handpiece,
a transmitter for transmitting outputs of the image sensor to the image processing unit, and
a second connector that mates with the first connector when said dental camera is being operated in the wireless mode; and a cable for operation during the wired mode, connected to the image processing unit, for supplying power to the handpiece and for delivering outputs of the image sensor to the image processing unit, the cable having a third connector that mates with the first connector when said dental camera is being operated in the wired mode.

11. The dental camera system as set forth in claim 10, wherein the image sensor comprises a charge-coupled device.

12. The dental camera system as set forth in claim 10, wherein the image sensor comprises an active pixel sensor array.

13. The dental camera system as set forth in claim 10, wherein the power supply comprises a rechargeable battery.

14. The dental camera as set forth in claim 10, wherein the first connector is located on a proximal end of the handpiece.

15. A dental camera switchable between a wireless mode and a wired mode, comprising:

a handpiece having means for generating a signal representing a video image and first connecting means;

a wireless adaptor module having power supply means for supplying power to the handpiece, transmitting means for transmitting the signal representing a video image, and second connecting means that mates with the first connecting means when said dental camera is being operated in the wireless mode; and a cable having third connecting means that mates with the first connecting means when said dental camera is being operated in the wired mode.

16. The dental camera as set forth in claim 15, wherein the transmitting means transmits the signal representing a video image to image processing means via a wireless link when said dental camera is being operated in the wireless mode.

17. The dental camera as set forth in claim 16, wherein the cable is connected to the image processing means when said dental camera is being operated in the wired mode.

18. The dental camera as set forth in claim 15, wherein the cable supplies power to the handpiece when said dental camera is being operated in the wired mode.

19. The dental camera as set forth in claim 15, wherein the first connector is located on a proximal end of the handpiece.

* * * * *